(12) United States Patent
Peretz

(10) Patent No.: US 10,527,614 B2
(45) Date of Patent: Jan. 7, 2020

(54) ASSAYS USING AVIDIN AND BIOTIN

(71) Applicant: Bio-Rad Laboratories, Inc., Hercules, CA (US)

(72) Inventor: David Peretz, Hercules, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 286 days.

(21) Appl. No.: 15/346,315

(22) Filed: Nov. 8, 2016

(65) Prior Publication Data

US 2017/0131269 A1    May 11, 2017

Related U.S. Application Data

(60) Provisional application No. 62/252,993, filed on Nov. 9, 2015.

(51) Int. Cl.
*G01N 33/50* (2006.01)
*G01N 33/543* (2006.01)
*G01N 33/58* (2006.01)

(52) U.S. Cl.
CPC . *G01N 33/54333* (2013.01); *G01N 33/54306* (2013.01); *G01N 33/58* (2013.01); *G01N 33/582* (2013.01)

(58) Field of Classification Search
None
See application file for complete search history.

(56) References Cited

U.S. PATENT DOCUMENTS

| 4,684,609 | A | 8/1987 | Hsu et al. |
| 6,680,208 | B1 | 1/2004 | Campos-Gonzalez et al. |
| 6,684,609 | B1 | 2/2004 | Bassissi et al. |
| 2009/0227044 | A1 | 9/2009 | Dosev et al. |
| 2010/0112716 | A1* | 5/2010 | Rosenzweig ......... B82Y 15/00 436/172 |
| 2012/0315621 | A1* | 12/2012 | Lu ........................... C12Q 1/34 435/5 |
| 2013/0065249 | A1 | 3/2013 | Tan et al. |
| 2014/0127719 | A1 | 8/2014 | Sheehan et al. |

FOREIGN PATENT DOCUMENTS

| CA | 2183204 A1 | 2/1997 |
| DE | 102010000906 A1 | 8/2010 |

OTHER PUBLICATIONS

International Search Report and Written Opinion from Application No. PCT/US2016/060987, dated Feb. 15, 2017, 10 pages.
Diamandis et al., "The Biotin-(Strept)Advidin System: Principles and Applications in Biotechnology",Clinical Chemistry, vol. 37, No. 5, pp. 625-636 (1991).
Hsu et al., "Use of Avidin-Biotin-Peroxidase Complex (ABC) in Immunoperoxidase Techniques", The Journal of Histochemistry and Cytochemistry, vol. 29, No. 4, pp. 577-580 (1981).
Guesdon, et al., "The Use of Avidin-Biotin Interaction in Immeunoenzymatic Techniques", The Journal of Histochemistry and Cytochemistry, vol. 27, No. 8, pp. 1131-1139 (1979).
European Patent App. No. EP16864861.6, Extended European Search Report dated Apr. 24, 2019.
Bio-Rad, "Bio-Rad Pro Human Inflammation Assays Instruction Manual," Oct. 2014.
Hsu, et al., "A Comparative Study of the Peroxidase-Antiperoxidase Method and an Avidin-Biotin Complex Method for Studying Polypeptide Hormones with Radioimmunoassay Antibodies," May 1981, Database Accession No. NLM6165237, "Abstract Only."

* cited by examiner

*Primary Examiner* — Gary Counts
(74) *Attorney, Agent, or Firm* — Kilpatrick Townsend and Stockton LLP

(57) ABSTRACT

The present disclosure provides methods and kits for detecting analytes using avidin-biotin assays.

14 Claims, 5 Drawing Sheets

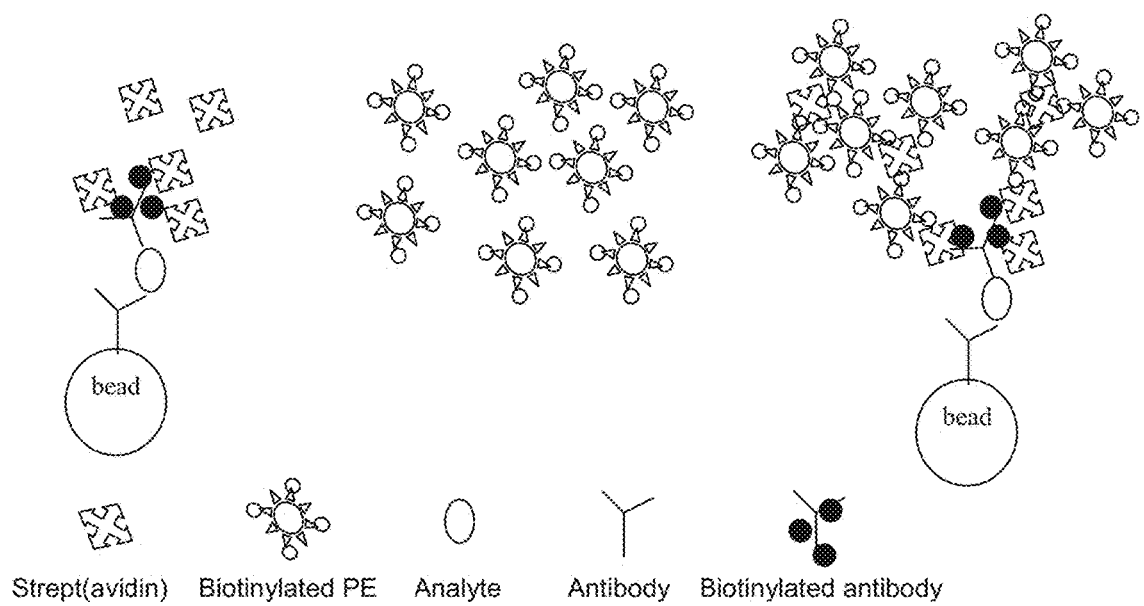
Figure 1. A schematic showing potential (strept)avidin – detectably labeled biotin interactions

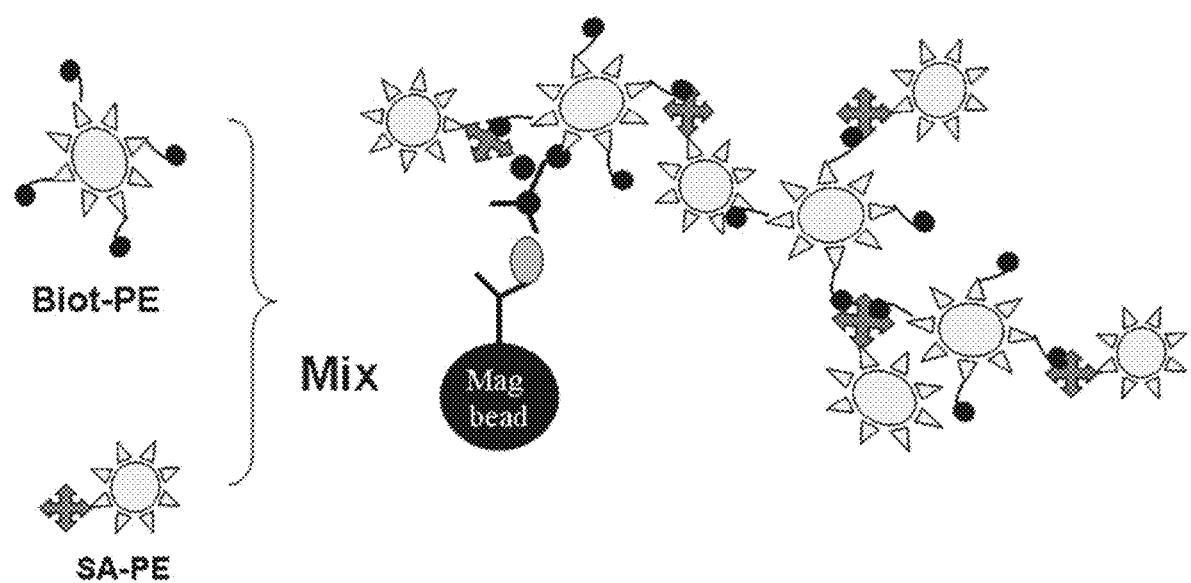
Figure 1A. A schematic showing potential detectably labeled (strept)avidin — detectably labeled biotin interactions

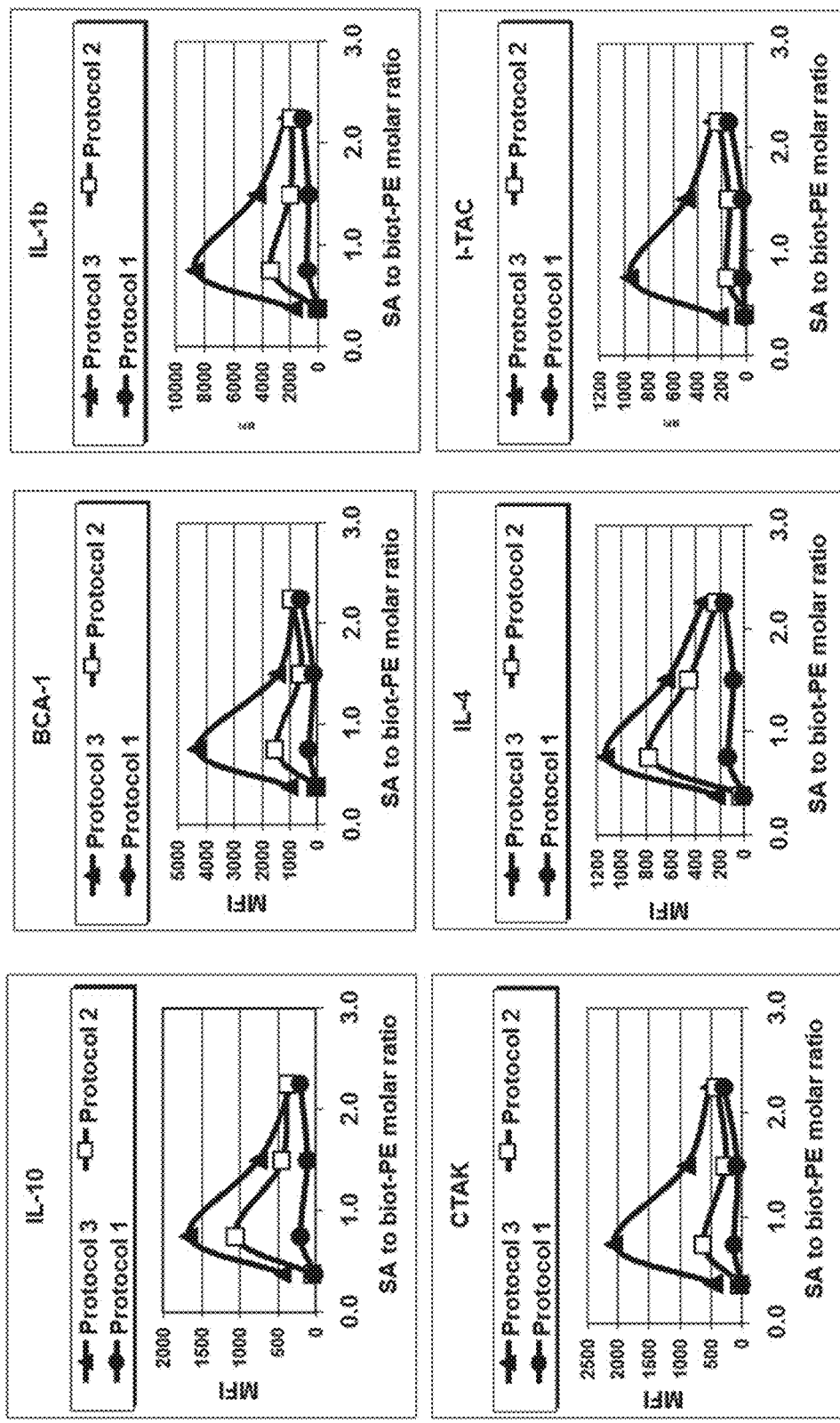
Figure 2. Representative assays using the three protocols.

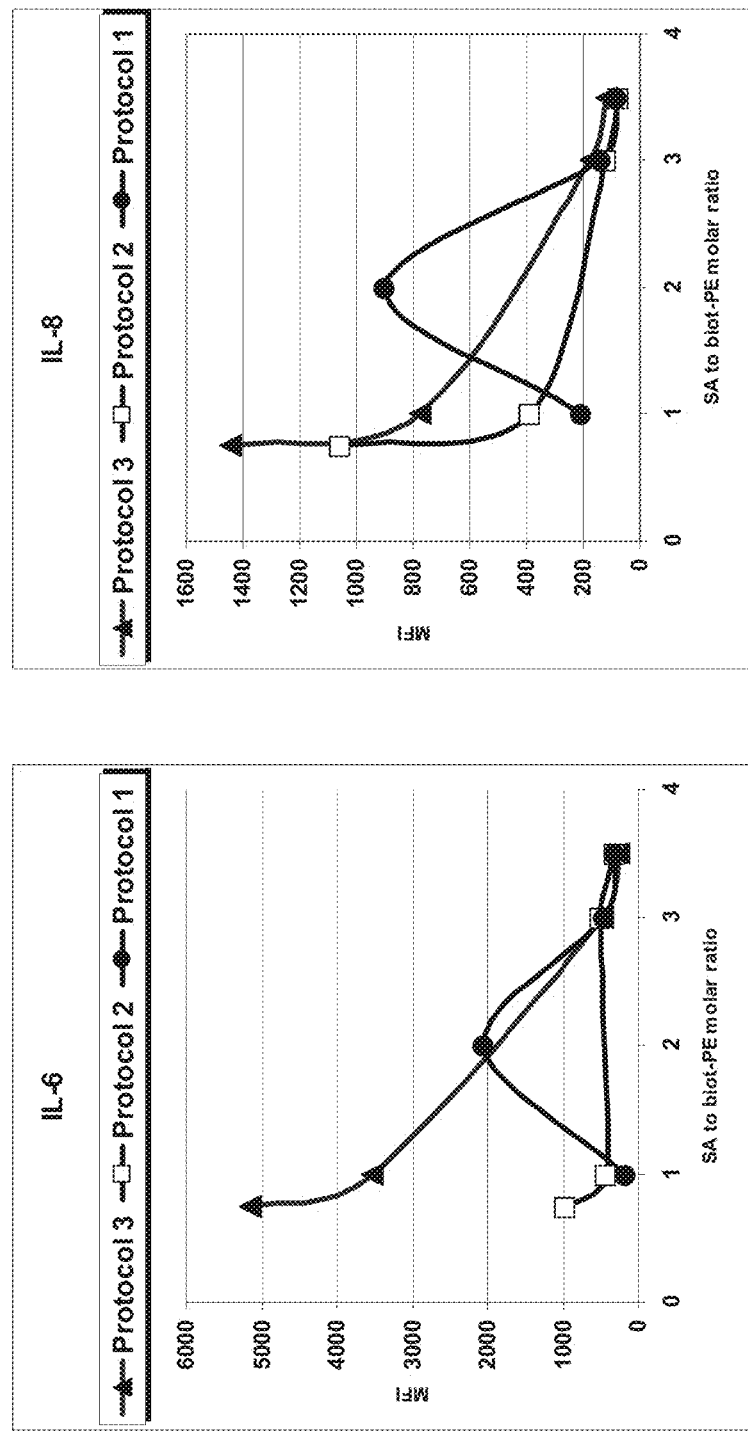
Figure 3. Effect of streptavidin to biotin – PE molar ratio on MFI.

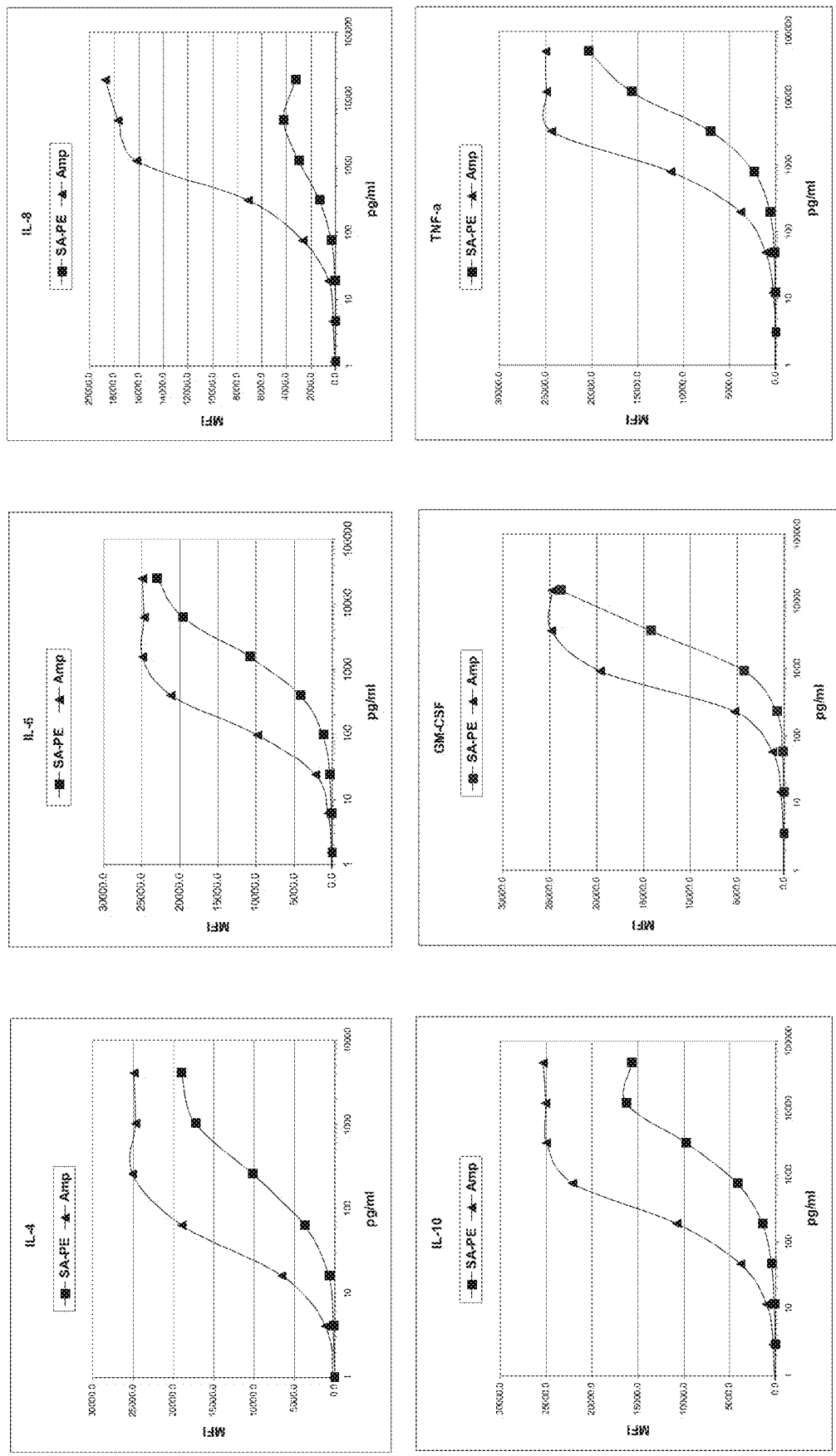
Figure 4. Comparison between standard BIO-PLEX protocol and the novel amplification protocol.

ASSAYS USING AVIDIN AND BIOTIN

CROSS-REFERENCE TO RELATED APPLICATIONS

This application claims priority from U.S. Provisional Application No. 62/252,993 filed on 9 Nov. 2015, contents of which are herewith incorporated by reference in its entirety.

BACKGROUND

The biotin-(strept)avidin system is a widely used detection system in a variety of different applications (Diamandis and Christopoulos (1991) Clin. Chem. 37: 625-36). Anti-immunoglobulins, protein A, protein G, lectins, enzymes, nucleotides, nucleic acids, hormones or cells have been avidin conjugated or biotinylated and used in various applications such as immunoassays, flow cytometry, immunohistochemistry, western blots, localization of receptors, microscopy, nucleic acid hybridization, affinity chromatography, receptor-ligand interactions and hybridoma production (Diamandis Tables 1 and 2, Supra).

The avidin-biotin interaction has been used for detecting a diverse number of targets with three basic configurations. In its simplest form, avidin or streptavidin, (referred herein sometimes as (strept)avidin)) is labeled with a detectable molecule, e.g., an enzyme, fluorescent, chemiluminescent, or radioactive probe; a metal; or some other moiety. Biotin present on another reactant (antibody, nucleotide, Protein A, lectin, etc.) links the target molecule with the labeling system. This detection format is used widely for immunoassays, DNA hybridization assays, immunohistochemistry, and flow-cytometry. Avidin and streptavidin conjugates carrying a variety of detectable molecules are commercially available.

In an indirect assay, (strept)avidin is used unlabeled and serves to link the biotinylated binding agent with the biotinylated detection molecule. This variation of the system takes advantage of the multiple biotin-binding sites in each avidin or streptavidin molecule. It is also used widely in immunoassay and DNA hybridization techniques, especially with probes that can be easily biotinylated (e.g., enzymes and proteinaceous fluorescent molecules).

The third method combines the principles of the above assays to yield a more sensitive system (Hsu et al. (1981) J. Histochem. Cytochem. 29, 577-80). The concept is to mix, under controlled conditions, unlabeled (strept)avidin and a biotinylated detection reagent, e.g., an enzyme. Given the multiple biotin binding sites on (strept)avidin, one can generate a polymer having some free biotin-binding sites. This reagent is then used as in the above assays but affords superior sensitivity. Kits offering the streptavidin or avidin and biotinylated enzymes at optimized concentrations, so that one can form the complex by simply mixing the reagents, are commercially available and are known as ABC (avidin-biotin complex) kits. In U.S. Pat. No. 4,684,609, Hsu et al disclose and claim that the weight ratio of avidin to biotinylated macromolecule is from 1:1 to 16:1; 1:6 to 16:1; and 2:1 to 4:1. Table 2 of the patent discloses data obtained by using avidin to biotinylated macromolecule with ratios 32:1, 16:1, 8:1, 4:1, 2:1, 1:1, 0.5:1, and 0.25:1. The data in Table 2 of the patent further indicate that avidin to biotinylated macromolecules at ratios of 32:1, 0.5:1 and 0.25:1 did not produce a detectable signal. Also of note is that ratios of 16:1, 8:1 and 4:1 at high avidin concentrations (40 mg/ml) resulted in higher background staining. The patent mentions that a preparation of the complex formed by mixing avidin and biotinylated macromolecule will remain active for a period of several days, at least (U.S. Pat. No. 6,684,609 at co.3, lines 43-44). Thus, several ratios need to be tried, every time, to determine optimum concentrations needed for a maximum signal generation. Moreover, the successful ratios described in the patent are generally useful wherein small complexes are needed, as in immunohistochemistry. A higher amplification signal using avidin-biotin system may allow increased detection range as well as use of less primary antibodies and antigen standards, thereby reducing the costs of the assay. Thus, there is a need in the art to develop novel assays providing these and other advantages.

SUMMARY

The disclosure relates to novel and improved analyte detection and/or quantitation assays and compositions using (strept)avidin-biotin detection system. In one embodiment, a method for detecting an analyte in a sample is disclosed, comprising: incubating the sample with a surface that is coated with a binding agent that binds to the analyte; incubating the surface with the same or a different binding agent of the analyte that is labeled with biotin; incubating the surface with (strept)avidin; without removing the (strept)avidin, further incubating the surface with a labeled biotin (e.g., biotin-fluorophore); washing the surface to remove reagents not bound to the surface; and detecting and/or quantitating the label and thereby detecting and/or quantitating the analyte.

In one aspect the surface is a bead, a magnetically responsive bead, a luminescent bead, or beads coated with different luminescence. In another aspect, the surface is a microtiter plate well, a protein or a nucleic acid transfer membrane, a biological cell, a microscopy slide or a microfluidic chip.

In one aspect, the molar ratio of (strept)avidin to labeled biotin is about 0.1:1 to 3:1. In a further aspect, the ratio is about 0.3:1 to 1:1.

In one aspect, biotin is labeled with a fluorophore, an enzyme, a radiolabel, an electron-dense reagent, a hapten or a protein. In one aspect, the fluorophore is phycoerythrin (PE). In another aspect, the enzyme is horse radish peroxidase or alkaline phosphatase.

In one aspect, streptavidin is labeled with a fluorophore, an enzyme, a radiolabel, an electron-dense reagent, a hapten or a protein. In one aspect, the fluorophore is phycoerythrin (PE). In another aspect, the enzyme is horse radish peroxidase or alkaline phosphatase.

In one aspect, (strept)avidin and biotin are both labeled with a fluorophore, an enzyme, a radiolabel, an electron-dense reagent, a hapten or a protein. In another aspect, (strept)avidin and biotin are labeled with the same fluorophore. In another aspect, (strept)avidin and biotin are labeled with different fluorophores. In one aspect, the fluorophore is phycoerythrin (PE). In another aspect, the enzyme is horse radish peroxidase or alkaline phosphatase.

In one embodiment, a kit is disclosed for a (strept)avidin-biotin assay, comprising, one or more bead sets coated with binding agent, detection antibodies labeled with biotin, (strept)avidin and/or biotin labeled with a fluorophore. In one embodiment, the fluorophore is phycoerythrin.

Additional aspects of the inventions are found elsewhere herein.

BRIEF DESCRIPTION OF THE DRAWINGS

FIG. 1 is a schematic showing potential (strept)avidin-labeled biotin interactions.

FIG. 1A is a schematic showing potential labeled (strept) avidin-labeled biotin interactions.

FIG. 2 shows results of representative assays using the three protocols.

FIG. 3 shows effect of streptavidin to biotin-PE molar ratio on MFI.

FIG. 4 shows comparison between standard BIO-PLEX™ protocol and the novel amplification protocol.

DETAILED DESCRIPTION

Unless defined otherwise, technical and scientific terms used herein have the same meaning as commonly understood by a person of ordinary skill in the art at the time the invention is made. See, e.g., Lackie, DICTIONARY OF CELL AND MOLECULAR BIOLOGY, Elsevier (4th ed. 2007); Sambrook et al., MOLECULAR CLONING, A LABORATORY MANUAL, Cold Spring Harbor Lab Press (Cold Spring Harbor, N.Y. 1989 and subsequent editions). The term "a" or "an" is intended to mean "one or more." The term "comprise," and variations thereof such as "comprises" and "comprising," when preceding the recitation of a step or an element, are intended to mean that the addition of further steps or elements is optional and not excluded. Any methods, devices and materials similar or equivalent to those described herein can be used in the practice of this invention. The following definitions are provided to facilitate understanding of certain terms used frequently herein and are not meant to limit the scope of the present disclosure.

DEFINITIONS

The terms "polypeptide," "peptide," and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers.

The term "binding agent" refers to a molecule that specifically binds to an antigen or analyte. Exemplary binding agents include, but are not limited to, an antibody, an antibody fragment, a non-antibody protein scaffold, an antibody mimetic, an aptamer, an affimer, a quenchbody, an antibody labeled with an enzyme, or an analyte-specific antibody pair.

The term "antibody" refers to a polypeptide of the immunoglobulin family or a polypeptide comprising fragments of an immunoglobulin that is capable of noncovalently, reversibly, and in a specific manner binding to a corresponding antigen. The term includes, but is not limited to, polyclonal or monoclonal antibodies of the isotype classes IgA, IgD, IgE, IgG, and IgM, derived from human or other mammalian cells, including natural or genetically modified forms such as humanized, human, single-chain, chimeric, synthetic, recombinant, hybrid, mutated, grafted, and in vitro generated antibodies. The term encompasses conjugates, including but not limited to fusion proteins containing an immunoglobulin moiety (e.g., chimeric or bispecific antibodies or single chain Fv's (scFv's)), and fragments, such as Fab, F(ab')2, Fv, scFv, Fd, dAb and other compositions.

The terms "antigen," "immunogen," "target," "analyte," and like terms are used herein to refer to a molecule, compound, or complex that is recognized by a binding agent, i.e., can be specifically bound by the binding agent. The term can refer to any molecule that can be specifically recognized by a binding agent, e.g., a protein, a polysaccharide, a toxin, a cell wall, a cell, a virus, a flagellum, a fimbria or pilus, a microorganism, a eukaryotic cell, a nucleic acid complexed to a protein or a polysaccharide, a lipid, a lipid complexed with a protein or a polysaccharide, a polynucleotide, a polypeptide, a carbohydrate, chemical moiety, or combinations thereof (e.g., phosphorylated or glycosylated polypeptides, etc.). One of skill will understand that the term does not indicate that the molecule is immunogenic in every context, but simply indicates that it can be targeted by a binding agent or an antibody.

Antibodies bind to an "epitope" on an antigen. The epitope is the localized site on the antigen that is recognized and bound by the antibody. Protein epitopes can include a few amino acids or portions of a few amino acids, e.g., 5 or 6, or more, e.g., 20 or more amino acids, or portions of those amino acids. Epitopes can also include non-protein components, e.g., nucleic acid (e.g., RNA or DNA), carbohydrate, or lipid or a combination thereof. In some cases, the epitope is a three-dimensional moiety. Thus, for example, where the target is a protein target, the epitope can be comprised of consecutive amino acids, or amino acids from different parts of the protein that are brought into proximity by protein folding (e.g., a discontinuous epitope). The same is true for other types of target molecules, such as DNA and chromatin, which form three-dimensional structures.

The terms "specific for," "specifically binds," and like terms refer to a molecule (e.g., binding agent) that binds to a target with at least 2-fold greater affinity than non-target compounds, e.g., at least 4-fold, 5-fold, 6-fold, 7-fold, 8-fold, 9-fold, 10-fold, 20-fold, 25-fold, 50-fold, or 100-fold greater affinity. For example, a binding agent that specifically binds a particular target will typically bind the target with at least a 2-fold greater affinity than a non-target.

The term "binds" with respect to a target (e.g., antigen, analyte, epitope), typically indicates that a binding agent binds a majority of the targets in a pure population, assuming an appropriate molar ratio of binding agent to target. For example, a binding agent that binds a given target typically binds to at least ⅔ of the targets in a solution (e.g., 75%, 80%, 85%, 90%, 91%, 92%, 93%, 94%, 95%, 96%, 97%, 98%, 99%, or 100%). One of skill will recognize that some variability will arise depending on the affinity of the binding agent for the target as well as method and/or threshold of determining binding.

The terms "label" and "detectable label" interchangeably refer to a composition detectable by spectroscopic, photochemical, biochemical, immunochemical, chemical, or other physical means. Useful labels include fluorescent dyes (fluorophores), fluorescent quenchers, luminescent agents, electron-dense reagents, enzymes (e.g., as commonly used in an ELISA), biotin, digoxigenin, $^{32}P$ and other radioisotopes, haptens, proteins, nucleic acids, or other substances which may be made detectable, e.g., by incorporating a label into an oligonucleotide, peptide, or antibody specifically reactive with a target molecule. The term includes combinations of single labeling agents, e.g., a combination of fluorophores that provides a unique detectable signature, e.g., at a particular wavelength or combination of wavelengths.

A molecule that is "linked" to a label (e.g., a labeled antibody as described herein) is one that is bound, either covalently, through a linker or a chemical bond, or noncovalently, through ionic, van der Waals, electrostatic, or hydrogen bonds to a label such that the presence of the molecule may be detected by detecting the presence of the label bound to the molecule.

"Multiplex assays" refer to analyses that simultaneously measure the levels of more than one analyte in a single reaction assay or vessel. Multiplex assay methods and reagents are described, e.g., in U.S. Pat. No. 6,773,578 and WO2008148883.

The term "solid support" or "surface" is used herein to denote a solid inert surface or body to which an agent, such as an antibody or an antigen can be immobilized. Non-limiting examples include plastic, nitrocellulose, membranes chips, and particles or beads. The term "immobilized" as used herein denotes a molecular-based coupling that is not significantly de-coupled under the conditions imposed during the steps of the assays described herein. Such immobilization can be achieved through a covalent bond, an ionic bond, an affinity-type bond, or any other chemical bond.

The term "particle" is used herein to refer to a solid or semisolid body, often with linear dimensions on the micron scale (i.e., less than 100 microns), of any shape or surface texture. Except as noted, the term is used interchangeably with "microparticle," which refers to a micron scale particle, and "bead," which refers to particles that are spherical or near-spherical in shape, often partially polymeric in composition.

"Biotin", a 244 Dalton vitamin found in tiny amounts in all living cells, binds with high affinity to avidin, streptavidin and Neutravidin™ proteins. Since biotin is a relatively small molecule, it can be conjugated to many proteins without significantly altering their biological activity. A protein can be reacted with several molecules of biotin that, in turn, can each bind a molecule of avidin. This greatly increases the sensitivity of many assay procedures. Biotin may further be labeled with a detection label, e.g., with a fluorophore or an enzyme.

"Avidin" is a glycoprotein found in the egg white and tissues of birds, reptiles and amphibians. It contains four identical subunits having a combined mass of 67,000-68,000 Daltons. Each subunit consists of 128 amino acids and binds one molecule of biotin. Another biotin-binding protein is "streptavidin", which is isolated from Streptomyces avidinii and has a mass of 75,000 Daltons. In contrast to avidin, streptavidin has no carbohydrate and has a mildly acidic pI (5.5). "Neutravidin"™ is a deglycosylated version of avidin, with a mass of approximately 60,000 Daltons. The terms avidin, streptavidin and (strept)avidin are used interchangeably herein. These avidins may further be labeled with a detection label, e.g., a fluorophore or an enzyme.

Assays

The indirect or bridged biotin-avidin-biotin assay first described by Guesdon (Guesdon et al., J. Histochem. Cytochem. 27: 1131-9 (1979), and followed in numerous protocols, is perhaps, less sensitive as it allows binding of only one or a very few molecules of avidin, because of steric hinderance, to a biotinylated antibody molecule. These protocols then wash away the unbound avidin before adding the labeled biotin. Thus, in these indirect methods further cross-linking of avidin with labeled biotin is unavailable.

The ABC (Avidin-Biotin Complex) method, on the other hand, has been shown to be more sensitive then the direct or indirect binding methods because of forming larger cross-linked complexes of streptavidin and labeled biotin. However, this perhaps results in a top-heavy molecular complex wherein a large lattice of avidin and labeled biotin is eventually tethered to a biotinylated antibody molecule bound to the antigen of interest. The complexes formed by the ABC method may not be very efficient as the spatial interference will limit the binding of large complexes to the biotinylated site. Also, a number of lattice complexes may have none of the binding sites of avidin available to bind to the analyte bound biotinylated antibody.

A novel approach, called "Amplification Protocol", is described herein to first allow (strept)avidin to bind to the biotinylated binding agent (e.g., antibody). The avidin-biotin complex is one of the strongest known non-covalent interaction ($K_d=10^{-15}$ M) between a protein and ligand. Therefore, adding (strept)avidin to the "surface bound binding agent-analyte-biotinylated binding agent" complex would ensure that every available biotin on the binding agent is bound by one or more (strept)avidin molecules. After suitable incubation time, e.g. 15-30 minutes, labeled biotin molecules are added, e.g., PE-biotin. It is only now that the free binding sites on (strept)avidin are being bound by PE-biotin, which in turn may form larger complexes with available avidin molecules. Not wishing to be bound by a theory, it is believed that these interactions may result in a more of a tree-like structure of the resulting complex and ensure that each biotinylated binding agent is bound by (strept)avidin which in turn are bound by one or more labeled biotinylated molecules, which further in turn are bound by (strept)avidin bound by labeled biotin. After suitable incubation time, the surface is washed. The washing step now gets rid of any unbound avidin or labeled biotin molecules and the surface is measured for the detectable signal. In one embodiment, the avidin is unlabeled. In a further embodiment, avidin is labeled.

In a further embodiment, both (strept)avidin and biotin are labeled with the same or different detectable labels, e.g., fluorophores. To differentiate from the above-described "amplification Protocol", the new protocol is referred to as "Dual Labeled Amplification Protocol" or DLAP or sometimes as "Amplification Protocol II". The dual- or multi-, if using more than two amplification steps, -amplification provides greater sensitivity and reduced use of reagents, particularly the primary antibodies against the target being detected. Use of different fluorophores on avidin and biotin may allow differentiation between direct biding versus amplification phase.

Sample

The assays and methods described herein can be used to detect one or more analytes in any type of sample. In some embodiments, the sample is a biological sample. In some embodiments, the sample may be a chemical or physical sample, e.g., water or a chemical solution or air or a rock. Biological samples can be obtained from any biological organism, e.g., an animal, plant, fungus, bacterial, viruses or prions or any other organism or the sample itself is an organism. In some embodiments, the biological sample is from an animal, e.g., a mammal (e.g., a human or a non-human primate, a cow, horse, pig, sheep, cat, dog, mouse, or rat), a bird (e.g., chicken), or a fish. A biological sample can be any tissue or bodily fluid obtained from the biological organism, e.g., blood, a blood fraction, or a blood product (e.g., serum, plasma, platelets, red blood cells, and the like), sputum or saliva, tissue (e.g., kidney, lung, liver, heart, brain, nervous tissue, thyroid, eye, skeletal muscle, cartilage, or bone tissue); cultured cells, e.g., primary cultures, explants, transformed cells, stem cells, stool, or urine.

In some embodiments, the one or more analytes to be detected are peptides, proteins (e.g., antibodies, enzymes, growth regulators, clotting factors, or phosphoproteins), immunogens, polysaccharides, toxins, cell walls, cell capsules, viral capsules, viral coats, flagellae, fimbriae or pili, microorganisms, nucleic acids complexed to protein or polysaccharide, or lipids complexed to protein or polysaccharide.

In some embodiments, two, three, four, five, or more different analytes may be detected. In some embodiments, wherein two or more different analytes are to be detected, the two or more different analytes are the same type of analytes (e.g., two or more proteins present in a complex). In some embodiments, wherein two or more different analytes are to be detected, the two or more different analytes are different types of analytes.

Binding Agent

A binding agent suitable for use according to the methods described herein is any molecule that specifically binds to an analyte (e.g., antigen) of interest. In some embodiments, the binding agent is an antibody or a portion thereof.

In some embodiments, the binding agent as described herein is linked to a detectable label. The label can be linked directly to the binding agent (e.g., by a covalent bond) or the attachment can be indirect (e.g., using a chelator or linker molecule). The terms "label" and "detectable label" are used interchangeably herein and are described in detail below.

Single Analyte Assays

The presently described assays may be performed as standalone single analyte assays as in a microtiter plates wells. The plates may be coated with a first binding agent that binds the analyte of interest in a sample. After washing the plate (wells), the assays are performed as described herein.

Multiplex Assays

The presently described assays are also capable of detecting one or more analyte in a single assay, and are thus described as multiplex assays. The presently described assays include components for immobilizing multiple analytes on distinguishable solid supports so that each of the multiple analytes can be identified and quantified by flow cytometry or other suitable means. Assay components and considerations include the solid supports and how to distinguish the different types of solid supports from one another (e.g., labels or other differentiation parameters), components to specifically immobilize the desired analytes and remove other sample materials, and labels for detecting and quantifying the desired analytes.

The presently described multiplex assays involve use of a solid support, typically particles (also referred to as microparticles or beads). For detection by flow cytometry, particles that emit autofluorescence should be avoided since this will increase background signal and may render them unsuitable. Particles created by standard emulsion polymerization from a variety of starting monomers generally exhibit low autofluorescence, while those that have been modified to increase porosity ("macroporous" particles) may exhibit high autofluorescence. Autofluorescence in such particles further increases with increasing size and increasing percentage of divinylbenzene monomer.

Within these limitations, the size range of the microparticles can vary and particular size ranges are not critical. In most cases, the aggregated size range of the microparticles lies within the range of from about 0.001 micrometers to about 100 micrometers in particle diameter, e.g., within the range of from about 0.5 micrometers to about 40 micrometers. The recently described nanoparticles are also suitable for these assays.

Magnetic particles are commonly used in the art, and can make separation and wash steps more convenient for the presently described assays. "Magnetic particles," "magnetically responsive material," "magnetic beads," and like terms denote a material that responds to a magnetic field. Magnetically responsive materials include paramagnetic materials (e.g., iron, nickel, and cobalt, as well as metal oxides such as $Fe_3O_4$, $BaFe_{12}O_{19}$, CoO, NiO, $Mn_2O_3$, $Cr_2O_3$, and CoMnP), ferromagnetic materials, ferrimagnetic materials, and metamagnetic materials. Rather than constituting the entire microparticle, the magnetically responsive material typically constitutes one component of the microparticle, while the remainder may consist of polymeric materials which may be chemically derivatized to permit attachment of an assay reagent (e.g., antigen or antibody).

Methods of, and instrumentation for, applying and removing a magnetic field as part of an assay are known to those skilled in the art and reported in the literature. Examples of literature reports are Forrest et al., U.S. Pat. No. 4,141,687; Ithakissios, U.S. Pat. No. 4,115,534; Vlieger et al., *Analytical Biochemistry* 205:1-7 (1992); Dudley, *Journal of Clinical Immunoassay* 14:77-82 (1991); and Smart, *Journal of Clinical Immunoassay* 15:246-251 (1992).

The polymeric matrix that forms the microparticle can be any material that is compatible with the presently described assays. The matrix should be inert to the components of the biological sample and to the assay reagents, have minimal autofluorescence, be solid and insoluble in the sample and in any other reagents or washes used in the assay, and capable of affixing an assay reagent to the microparticle. Non-limiting examples of suitable polymers are polyesters, polyethers, polyolefins, polyalkylene oxides, polyamides, polyurethanes, polysaccharides, celluloses, and polyisoprenes. Crosslinking is useful in many polymers for imparting structural integrity and rigidity to the microparticle.

Functional groups for attachment of the assay reagent (e.g., antigen or antibody) can be incorporated into the polymer structure by conventional means. Non-limiting examples of suitable functional groups are amine groups, ammonium groups, hydroxyl groups, carboxylic acid groups, and isocyanate groups. The assay reagent is typically covalently bound to the solid phase surface, either directly or indirectly, e.g., with a linking group. Linking groups can be used as a means of increasing the density of reactive groups on the solid phase surface and decreasing steric hindrance to increase the range and sensitivity of the assay, or as a means of adding specific types of reactive groups to the solid phase surface to broaden the range of types of assay reagents that can be affixed to the solid phase. Non-limiting examples of suitable useful linking groups are polylysine, polyaspartic acid, polyglutamic acid and polyarginine.

Microparticles of different types in a multiplex assay can be distinguished from one another, e.g., by size, weight, light scatter or absorbance, reflectance, shape, or label, e.g., fluorescent label.

Where microparticle size is used as a differentiation factor (distinguishing characteristic), the widths of the size subranges and the spacing between mean diameters of adjacent subranges are selected to permit differentiation of different types of microparticles by flow cytometry, as will be apparent to those skilled in the use of and instrumentation for flow cytometry. Typically, a subrange for a given mean diameter is about ±5% CV or less of the mean diameter, where CV is the coefficient of variation and is defined as the standard deviation of the particle diameter divided by the mean particle diameter times 100 percent. The mean diameters of subranges for different types of particles are generally spaced apart by at least about 6% of the mean diameter of one of the subranges, e.g., at least about 8% or 10% of the mean diameter of one of the subranges.

Light scatter can also be used to distinguish different types of microparticles. Side angle light scatter varies with particle size, granularity, absorbance and surface roughness, while forward angle light scatter is mainly affected by size and refractive index. Varying any of these qualities can result in light scatter differences that can serve as a means of distinguishing the various groups.

Still another example of a differentiation parameter is absorbance. When light is applied to particles, the absorbance of the light by the particles is indicated mostly by a change in the strength of the laterally (side-angle) scattered light while the strength of the forward-scattered light is relatively unaffected. Consequently, the difference in absorbance between various colored dyes associated with the particles is determined by observing differences in the strength of the laterally scattered light.

A wide array of parameters or characteristics can be used as differentiation parameters to distinguish the particles of one group from those of another. The differentiation parameters may arise from particle size, composition, physical characteristics that affect light scattering, excitable fluorescent dyes or colored dyes that impart different emission spectra and/or scattering characteristics to the particles, or from different concentrations of one or more fluorescent dyes.

When the distinguishable characteristic is a fluorescent dye or color, it can be coated on the surface of the microparticle, embedded in the microparticle, or bound to the molecules of the microparticle material. Thus, fluorescent microparticles can be manufactured by combining the polymer material with the fluorescent dye, or by impregnating the microparticle with the dye. Microparticles with dyes already incorporated and thereby suitable for use in the present invention are commercially available, from suppliers such as Spherotech, Inc. (Libertyville, Ill., USA) and Molecular Probes, Inc. (Eugene, Oreg., USA). A list of vendors of flow cytometry products can be found, e.g., on the world wide web at molbiol.princeton.edu/facility/flow-cyt/.

Examples of detectable labels include, but are not limited to, biotin/streptavidin labels (further described below), nucleic acid (e.g., oligonucleotide) labels, chemically reactive labels, fluorescent labels, enzyme labels, radioactive labels, quantum dots, polymer dots, mass labels, and combinations thereof. In some embodiments, the label can include an optical agent such as a fluorescent agent, phosphorescent agent, chemiluminescent agent, etc. Numerous agents (e.g., dyes, probes, or indicators) are known in the art and can be used in the present invention. (See, e.g., Invitrogen, The Handbook—A Guide to Fluorescent Probes and Labeling Technologies, Tenth Edition (2005)). Fluorescent agents can include a variety of organic and/or inorganic small molecules or a variety of fluorescent proteins and derivatives thereof. Literature sources for fluorophores include Cardullo et al., *Proc. Natl. Acod. Sci. USA* 85: 8790-8794 (1988); Dexter, *J. of Chemical Physics* 21: 836-850 (1953); Hochstrasser et al., *Biophysical Chemistry* 45: 133-141 (1992); Selvin, *Methods in Enzymology* 246: 300-334 (1995); Steinberg, *Ann. Rev. Biochem.*, 40: 83-114 (1971); Stryer, *Ann. Rev. Biochem.* 47: 819-846 (1978); Wang et al., *Tetrahedron Letters* 31: 6493-6496 (1990); and Wang et al., *Anal. Chem.* 67: 1197-1203 (1995). Fluorescent dyes and fluorescent label reagents include those which are commercially available, e.g., from Invitrogen/Molecular Probes (Eugene, Oreg.) and Pierce Biotechnology, Inc. (Rockford, Ill.).

The following are non-limiting examples of fluorophores that can be used as labels: 4-acetamido-4'-isothiocyanatostilbene-2,2'disulfonic acid, acridine, acridine isothiocyanate, 5-(2'-aminoethyl)aminonaphthalene-1-sulfonic acid (EDANS), 4-amino-N-[3-vinylsulfonyl)phenyl]naphthalimide-3,5 disulfonate, N-(4-anilino-1-naphthyl)maleimide, anthranilamide, BODIPY, Brilliant Yellow, coumarin, 7-amino-4-methylcoumarin (AMC, Coumarin 120), 7-amino-4-trifluoromethylcoumarin (Coumaran 151), cyanine dyes, cyanosine, 4',6-diaminidino-2-phenylindole (DAPI), 5',5'''-dibromopyrogallol-sulfonaphthalein (Bromopyrogallol Red), 7-diethylamino-3-(4'-isothiocyanatophenyl)-4-methylcoumarin, diethylenetriamine pentaacetate, 4,4'-diisothiocyanatodihydro-stilbene-2,2'-disulfonic acid, 4,4'-diisothiocyanatostilbene-2,2'-disulfonic acid, 5-[dimethylamino]naphthalene-1-sulfonyl chloride (DNS, dansylchloride), 4-(4'-dimethylaminophenylazo)benzoic acid (DABCYL), 4-dimethylaminophenylazophenyl-4'-isothiocyanate (DABITC), eosin, eosin isothiocyanate, erythrosin B, erythrosin isothiocyanate, ethidium, 5-carboxyfluorescein (FAM), 5-(4,6-dichlorotriazin-2-yl) aminofluorescein (DTAF), 2',7'-dimethoxy-4'5'-dichloro-6-carboxyfluorescein (JOE), fluorescein, fluorescein isothiocyanate, fluorescamine, IR144, IR1446, Malachite Green isothiocyanate, 4-methylumbelliferone, ortho cresolphthalein, nitrotyrosine, pararosaniline, Phenol Red, phycoerythrin (including but not limited to B and R types), o-phthaldialdehyde, pyrene, pyrene butyrate, succinimidyl 1-pyrene butyrate, quantum dots, Reactive Red 4 (Cibacron™ Brilliant Red 3B-A), 6-carboxy-X-rhodamine (ROX), 6-carboxyrhodamine (R6G), lissamine rhodamine B sulfonyl chloride rhodamine, rhodamine B, rhodamine 123, rhodamine X isothiocyanate, sulforhodamine B, sulforhodamine 101, sulfonyl chloride derivative of sulforhodamine 101 (Texas Red), N,N,N',N'-tetramethyl-6-carboxyrhodamine (TAMRA), tetramethyl rhodamine, tetramethyl rhodamine isothiocyanate (TRITC), riboflavin, rosolic acid, lanthanide chelate derivatives. In some embodiments, the optical agent is an intercalating dye. Intercalating dyes include, but are not limited to, SYBR Green and Pico Green (from Molecular Probes, Inc., Eugene, Oreg.), ethidium bromide, propidium iodide, chromomycin, acridine orange, Hoechst 33258, TOTO-I, YOYO-1, and DAPI (4',6-diamidino-2-phenylindole hydrochloride).

A routinely used group of fluorophores for immunoassays are fluorescein, fluorescein isothiocyanate, phycoerythrin, rhodamine B, and Texas Red (sulfonyl chloride derivative of sulforhodamine 101). Any of the fluorophores in the list preceding this paragraph can be used in the presently described assays, either to label the microparticle, or to label a binding agent (e.g., an antibody or streptavidin). Fluorochromes can be attached by conventional covalent bonding, using appropriate functional groups on the fluorophores and on the microparticle or binding agent. The recognition of such groups and the reactions to form the linkages will be readily apparent to those skilled in the art.

In some embodiments, a fluorescent agent is a polymer dot or a quantum dot. The particular quantum dot (QD) employed is not critical to the present invention. Quantum dots are known in the art and are described, for example, by Han et al., "Quantum-dot-tagged Microbeads for Multiplexed Optical Coding of Biomolecules", Nat Biotechnol (July 2001) vol. 19, pp. 631-635. One of skill in the art will appreciate the various quantum dots that may serve as fluorescent labels and that can be employed in embodiments of the invention and which are available from various commercial vendors. Exemplary quantum dots (QDs) include, but are not limited to, the following: cadmium selenide (CdSe) quantum dot nanoparticles (e.g., CdSe Quantum Dot Cores, 480-640 nm emission spectra, Sigma-Aldrich®); cadmium sulfide (CdS) quantum dot nanoparticles (e.g., CdS Quantum Dot Cores, 380-480 nm emission spectra, Sigma-Aldrich®); zinc sulfide-capped cadmium selenide (ZnS-capped CdSe) nanocrystals (e.g., CdSe/ZnS Lumidots™ and CdSe/ZnS NanoDots™, 480-640 nm emission spectra, Sigma-Aldrich®); and cadmium-free quantum dots (e.g., CFQD™, 400-650 nm emission spectra, Sigma-Aldrich®).

Techniques for attaching detectable labels to binding agents are known. For example, a review of common protein labeling techniques can be found in Biochemical Techniques: Theory and Practice, John F. Robyt and Bernard J. White, Waveland Press, Inc. (1987). Other labeling techniques are reviewed in, e.g., R. Haugland, Excited States of Biopolymers, Steiner ed., Plenum Press (1983); Fluorogenic Probe Design and Synthesis: A Technical Guide, PE Applied Biosystems (1996); and G. T. Herman, Bioconjugate Techniques, Academic Press (1996). The techniques are also available as parts of commercially available kits (e.g., Thunder-Link® and Lightning-Link® from Innova Biosciences Ltd., Cambridge, United Kingdom). Many suitably labeled binding agents are commercially available and may be used with or without further modifications.

Other labels that can be used in place of the fluorophores are radioactive labels and enzyme labels. These are likewise known in the art.

Flow cytometry methods and instrumentation are known in the art. Descriptions of instrumentation and methods can be found, e.g., in Introduction to Flow Cytometry: A Learning Guide (2000) Becton, Dickinson, and Company; McHugh, "Flow Microsphere Immunoassay for the Quantitative and Simultaneous Detection of Multiple Soluble Analytes," Methods in Cell Biology 42, Part B (Academic Press, 1994).

Kits

In another aspect, kits for detecting an analyte according to the methods described herein are provided. In some embodiments, a kit comprises one or more binding agents, e.g., one or more antibodies labeled with biotin, and/or analyte-specific antibody pair, (strept)avidin, labeled biotin, e.g., phycoerythrin labeled biotin, beads, control reagents, as described herein. In some embodiments, a kit further comprises assay components (e.g., buffers, buffer salts, and/or surfactants). In some embodiments, a kit for detecting an analyte further comprises the analyte to which the binding specifically binds. In some embodiments, a kit further comprises instructions for carrying out the methods described herein.

Systems

Also provided are systems for performing the methods described herein. The assays and methods may be performed in an ELISA-like setting using plate readers or may be used with multiplex systems. For example, BIO-PLEX™ 200 BIO-PLEX™ MAGPIX systems from BIO-RAD, or Luminex 200™, FLEXMAP 3D® from Luminex Corporation may be used to conduct the methods of the invention. The assays are also suitable for use in Western blot setting as well as protein/antibody arrays or microfluidic devices. Any and all analyte detection system that uses direct or indirect (strept)avidin-biotin detection system, can be modified to use the amplification protocol described herein to increase sensitivity.

EXAMPLES

Example 1

Here we describe a novel signal amplification protocol. In this protocol we first attempt to saturate antibody-biotin sites with (strept)avidin before adding biotinylated PE (or other suitable label), to generate large fluorescence complexes.

BIO-PLEX™ workflow protocol is available from Bio-Rad, Hercules, Calif. and is briefly summarized below.

In brief: 30 min incubation of standards or sample with beads coated with the capture antibody—wash—30 min incubation with detection antibody—wash—30 min incubation with avidin-PE—wash—read on BIO-PLEX™ system.

In order to increase the sensitivity of the (strept)avidin-biotin-based assays, we decided to amplify the signal by using unlabeled avidin and biotinylated PE after the binding by the detection antibody to the beads. We have tried the following three amplification protocols using BIO-PLEX Pro™ Human Chemokine Panel, 40-Plex (Bio-Rad laboratories, Hercules, Calif.).

Protocol 1) biotinylated PE and streptavidin were mixed, allowed to form complexes and then were added to the magnetic beads after the detection antibody incubation, a protocol similar to the immunohistochemistry protocol (comparable to U.S. Pat. No. 4,684,609).

Protocol 2) streptavidin, biotinylated-PE and magnetic beads after the detection antibody incubation, were all together.

Protocol 3) streptavidin was first incubated with magnetic beads after the detection antibody incubation, for 15 minutes and biotinylated PE was added without removing streptavidin. These protocols were tested at different ratios of streptavidin to biotinylated-PE. Six representative graphs are shown in FIG. 2.

We find that the novel Protocol 3 generates more fluorescence units (MFI, median fluorescence intensity) than Protocol 1 where complexes are pre-formed prior to binding or Protocol 2 where complexes are forming concurrently while binding the antibody. This perhaps suggests that formation of complexes prior to or concurrent with the antibody binding may not be appropriate where increased assay sensitivity is desired. Consistent with the disclosure in the U.S. Pat. No. 4,684,609, the optimum molar ratio of streptavidin to biotin-probe for Protocol 1 is about 2. However, we find that optimal molar ratio for Protocol 3 is only about 0.75 indicating a mechanism of complex formation that may be different from protocols 1 and 2. It is possible that there are many non-productive complexes (e.g., if all four of the (strept)avidin binding sites are already occupied by biotin-PE), formed in Protocols 1 and 2 that do not get an opportunity to bind the biotinylated antibody. Not wishing to be bound by theory, and as one of the many possibilities only, we envision the complex formation as depicted in FIG. 1. However, there may be (are) other complex formation possibilities not described by FIG. 1 that may be at play here. Table 1 provides further examples from this experiment.

TABLE 1

Examples of BIO-PLEX Pro™ Human Chemokine Panel, 40-Plex

| | | | IFN-g | | IL-10 | | IL-8 | | IL-1b | | IL-2 | | IL-4 | | IL-6 | |
|---|---|---|---|---|---|---|---|---|---|---|---|---|---|---|---|---|
| Amp protocol | ug/ml | Sample | FI | % CV | FI | % CV | FI | % CV | FI | % CV | FI | % CV | FI | % CV | FI | % CV |
| Protocol 1 Mix | SA 1 | QC | 8 | 0 | 16 | 0 | 64 | 4 | 17 | 0 | 9 | 0 | 10 | 0 | 11 | 0 |
| SA and biot- | PE 12 | Blank | 7 | 11 | 9 | 4 | 7 | 11 | 7 | 11 | 6 | 0 | 6 | 0 | 6 | 13 |
| PE for 15 min | SA 2 | QC | 36 | 7 | 198 | 1 | 1817 | 4 | 762 | 0 | 65 | 8 | 135 | 12 | 218 | 1 |
| then add to | PE 12 | Blank | 8 | 9 | 10 | 7 | 7 | 20 | 7 | 20 | 7 | 11 | 6 | 0 | 7 | 11 |
| beads for | SA 4 | QC | 14 | 0 | 112 | 4 | 301 | 5 | 696 | 14 | 64 | 12 | 91 | 18 | 164 | 14 |
| another 15 min | PE 12 | Blank | 7 | 20 | 9 | 8 | 6 | 0 | 7 | 11 | 7 | 20 | 6 | 0 | 6 | 13 |
| | SA 6 | QC | 53 | 7 | 206 | 0 | 667 | 4 | 1086 | 7 | 237 | 3 | 166 | 10 | 423 | 2 |
| | PE 12 | Blank | 7 | 5 | 11 | 7 | 9 | 8 | 7 | 0 | 9 | 0 | 9 | 8 | 7 | 0 |
| Protocol 2 Mix | SA 1 | QC | 12 | 0 | 41 | 0 | 227 | 0 | 62 | 1 | 16 | 9 | 23 | 6 | 30 | 2 |
| SA and biot- | PE 12 | Blank | 7 | 0 | 9 | 16 | 7 | 11 | 7 | 11 | 7 | 11 | 7 | 33 | 6 | 13 |
| PE for 30 min | SA 2 | QC | 177 | 1 | 1063 | 8 | 5685 | 2 | 3359 | 10 | 360 | 15 | 771 | 23 | 1029 | 9 |
| with beads | PE 12 | Blank | 8 | 9 | 11 | 7 | 8 | 18 | 7 | 20 | 9 | 8 | 7 | 11 | 8 | 5 |
| | SA 4 | QC | 40 | 8 | 446 | 10 | 916 | 0 | 1979 | 18 | 304 | 9 | 454 | 16 | 512 | 6 |
| | PE 12 | Blank | 7 | 0 | 10 | 14 | 8 | 0 | 7 | 11 | 8 | 0 | 6 | 6 | 7 | 0 |
| | SA 6 | QC | 76 | 0 | 375 | 13 | 920 | 12 | 1899 | 8 | 299 | 3 | 227 | 9 | 623 | 6 |
| | PE 12 | Blank | 8 | 9 | 11 | 7 | 9 | 8 | 8 | 28 | 8 | 5 | 8 | 14 | 10 | 14 |
| Protocol 3 Mix | SA 1 | QC | 75 | 2 | 430 | 4 | 967 | 6 | 1734 | 1 | 185 | 2 | 233 | 4 | 461 | 3 |
| SA with beads | PE 12 | Blank | 8 | 0 | 15 | 9 | 10 | 4 | 9 | 0 | 13 | 3 | 15 | 5 | 24 | 7 |
| with for 15 min | SA 2 | QC | 207 | 3 | 1667 | 0 | 3506 | 2 | 8721 | 6 | 549 | 6 | 1123 | 10 | 1739 | 7 |
| then biot-PE | PE 12 | Blank | 11 | 13 | 18 | 16 | 16 | 20 | 13 | 28 | 20 | 25 | 20 | 11 | 41 | 30 |
| for 15 min | SA 4 | QC | 123 | 11 | 765 | 9 | 1112 | 5 | 4366 | 10 | 282 | 8 | 634 | 15 | 664 | 15 |
| | PE 12 | Blank | 12 | 6 | 26 | 22 | 17 | 4 | 19 | 60 | 27 | 5 | 34 | 4 | 62 | 5 |
| | SA 6 | QC | 59 | 23 | 313 | 6 | 982 | 6 | 2307 | 22 | 147 | 8 | 338 | 11 | 481 | 18 |
| | PE 12 | Blank | 11 | 26 | 24 | 66 | 25 | 68 | 16 | 50 | 28 | 80 | 25 | 56 | 61 | 69 |

FI—fluorescence intensity;
% CV—% coefficient of variation;
SA—Streptavidin;
PE—biotinylated
R—phycoerythrin Based on the above observations, further experiments were performed using Protocol 3, also referred to as "Amplification Protocol", interchangeably.

Example 2

In another set of studies the molar ratio of streptavidin to biotin-PE was increased to more than three and again the novel protocol was superior to protocols 1 and 2 and exhibited highest MFI at about 0.75:1 (strept)avidin to biotin-PE molar ratio (FIG. 3).

Example 3

Next the performance of the Amplification Protocol was compared to the standard BIO-PLEX™ protocol (using streptavidin-PE), using a Human cytokine multiplex panel detection assays for IL-4, IL-6, IL-8, IL-10, GM-CSF, and TNF-alpha. The protocols were tested against standard curve made of recombinant proteins. Both assays were run at the same day on the same plate. We observed stronger fluorescence signal from assays done with the Amplification Protocol (FIG. 4). For example saturation for IL-4 with the standard BIO-PLEX™ protocol is at about 4,000 pg/ml while for the Amplification Protocol it is at about 200 pg/ml. It should be noted that only 60 pg/ml is needed to reach the saturation limit of standard protocol when using the Amplification Protocol. Similarly, for IL-6 the fluorescence reaches to maximum of about 25,000 MFI with 30,000 pg/ml using the standard BIO-PLEX™ protocol while with the Amplification Protocol it reaches the same maximum with only 2,000 pg/ml.

This increase in signal translates to better Limit of Quantification (LOQ) values as determined with Bio-Rad's BIO-PLEX™ Manager software. Improvements in signal amplification using the Amplification Protocol ranged from 2 to 15 fold over standard BIO-PLEX™ protocol suggesting increase in assay sensitivity (Table 2).

To assess the detection of these proteins in their natural settings, we measured the amount of these cytokines in growth medium of THP-1 cells treated with lipopolysaccharide (LPS) for 24 h (Table 3). IL-4 was only detected after using the signal amplification procedure. All other cytokines were abundant and detected by both protocols. Significantly, for these targets, the amplification protocol yielded values similar to the standard assays suggesting that the amplification protocol did not introduce notable bias in the quantification.

These data demonstrate some of the advantages of using the amplification protocol over the standard assay. The amplification procedure improves assay sensitivity as evidenced by the detection of IL-4 in the media of THP-1 cells (Table 3) and by lower LOQ values (Table 2). The amplification procedure can potentially lead to cost savings in materials as much lower concentration of recombinant antigens are needed to reach standard curve saturation as well as the amount of detection antibodies needed to match the MFI generated by the standard protocol.

TABLE 2

HU Cytokine Panel

| Cytokine | SA-PE | Amplification |
|---|---|---|
| | LOQ (pg/ml) | |
| IL-4 | 0.2 | 0.1 |
| IL-6 | 0.5 | 0.1 |

TABLE 2-continued

HU Cytokine Panel

| Cytokine | SA-PE LOQ (pg/ml) | Amplification LOQ (pg/ml) |
|---|---|---|
| IL-8 | 1.2 | 0.3 |
| IL-10 | 3.0 | 0.2 |
| GM-CSF | 4.3 | 1.0 |
| TNF-alpha | 3.0 | 0.2 |

TABLE 3

THP-1 LPS 24 h cell culture media

| Cytokine | SA-PE pg/ml | Amplification pg/ml |
|---|---|---|
| IL-4 | 0 | 1 |
| IL-6 | 126 | 138 |
| IL-8 | Too high | Too high |
| IL-10 | 7 | 10 |

TABLE 3-continued

THP-1 LPS 24 h cell culture media

| Cytokine | SA-PE pg/ml | Amplification pg/ml |
|---|---|---|
| GM-CSF | 9 | 10 |
| TNF-alpha | 493 | 643 |

Example 4

In a further variation, the streptavidin reagent was labeled with PE. This creates a double amplification (amplification II), as both streptavidin and subsequent biotin are labeled with a fluorophore that fluoresces at the same wavelength. An enzyme, e.g., HRP, may be used similarly. In this study we compared the fluorescence intensity (FI) of the three protocols; Bio-Plex™, and signal amplifications versions I and II. The study was done with multiplex of eight human assays against recombinant proteins at different concentrations outline in Table 4.

TABLE 4

8-plex human cytokine panel

| Protein standards | IL-2 pg/ml | IL-4 pg/ml | IL-6 pg/ml | IL-8 pg/ml | IL-10 pg/ml | GM-CSF pg/ml | IFN-g pg/ml | TNF-a pg/ml |
|---|---|---|---|---|---|---|---|---|
| 1 | 72 | 19 | 151 | 178 | 142 | 52 | 111 | 266 |
| 2 | 5 | 1 | 9 | 11 | 9 | 3 | 7 | 17 |
| 3 | 0.3 | 0.1 | 0.6 | 0.7 | 0.6 | 0.2 | 0.4 | 1.0 |
| Blank | 0 | 0 | 0 | 0 | 0 | 0 | 0 | 0 |

The reagents column in Table 5 outlines the concentration of the signal amplification reagents. The readout demonstrates the increase in fluorescence with the amplification protocols with version II exhibiting higher fluorescence than Bio-PLEX™ or amplification I protocol.

TABLE 5

| Assay | Reagents | Time min | Protein stds | IL-2 FI | IL-2 % CV | IL-4 FI | IL-4 % CV | IL-6 FI | IL-6 % CV | IL-8 FI | IL-8 % CV | IL-10 FI | IL-10 % CV | GM-CSF FI | GM-CSF % CV | IFN-g FI | IFN-g % CV | TNF-a FI | TNF-a % CV |
|---|---|---|---|---|---|---|---|---|---|---|---|---|---|---|---|---|---|---|---|
| Bio-Plex | SA-PE 50 ul at 2 ug/ml | 10 | 1 | 679 | 5 | 418 | 4 | 558 | 0 | 264 | 5 | 465 | 3 | 153 | 7 | 53 | 4 | 249 | 2 |
|  |  |  | 2 | 52 | 6 | 35 | 2 | 45 | 9 | 24 | 6 | 47 | 2 | 28 | 3 | 13 | 0 | 26 | 0 |
|  |  |  | 3 | 18 | 0 | 17 | 4 | 12 | 0 | 10 | 7 | 17 | 4 | 21 | 13 | 10 | 7 | 11 | 0 |
|  |  |  | Blank | 17 | 13 | 15 | 2 | 10 | 0 | 8 | 0 | 15 | 9 | 20 | 4 | 10 | 7 | 11 | 7 |
| Signal Amplification I | SA 25 ul at 2 ug/ml; biot-PE 25 ul at 12 ug/ml | 15 15 | 1 | 1588 | 4 | 1319 | 2 | 1676 | 6 | 707 | 5 | 1487 | 5 | 566 | 16 | 121 | 13 | 685 | 5 |
|  |  |  | 2 | 113 | 3 | 104 | 1 | 138 | 2 | 66 | 5 | 168 | 2 | 58 | 4 | 28 | 0 | 54 | 12 |
|  |  |  | 3 | 25 | 3 | 40 | 5 | 26 | 7 | 24 | 10 | 30 | 2 | 39 | 4 | 19 | 2 | 18 | 8 |
|  |  |  | Blank | 21 | 2 | 33 | 0 | 17 | 0 | 23 | 11 | 18 | 10 | 42 | 3 | 20 | 4 | 16 | 5 |
| Signal Amplification II | SA-PE 25 ul at 16 ug/ml; biot-PE 25 ul at 6 ug/ml | 15 15 | 1 | 8630 | 2 | 5590 | 1 | 5941 | 8 | 2496 | 7 | 14262 | 12 | 2388 | 2 | 296 | 20 | 4956 | 6 |
|  |  |  | 2 | 518 | 10 | 323 | 15 | 468 | 16 | 204 | 11 | 1138 | 2 | 234 | 8 | 57 | 6 | 310 | 1 |
|  |  |  | 3 | 75 | 8 | 62 | 8 | 60 | 21 | 56 | 13 | 138 | 13 | 126 | 1 | 43 | 32 | 35 | 9 |
|  |  |  | Blank | 39 | 6 | 50 | 7 | 28 | 3 | 43 | 25 | 65 | 16 | 109 | 22 | 36 | 18 | 21 | 5 |

Stds—standards

Example 5

Three BIO-PLEX™ assays were tested with two protocols, the standard BIO-PLEX™ and the signal amplification version II. Each assay was run with 10 standard curve points including blank. Samples tested were human serum spiked with recombinant antigen and plasma samples pooled from cardio vascular disease (CVD), rheumatoid arthritis (RA), and systemic lupus erythematosus (SLE) patients. The samples were diluted four times before testing and protein concentration was extrapolated from the standard curve. The detection antibody in the signal amplification protocol was diluted four times to lower background. In all three assays (Tables 6, 7, and 8), the signal amplification protocol is more sensitive than the current BIO_PLEX™ protocol enabling the user to detect protein targets that otherwise will not have been detected as well as reducing the reagent costs.

TABLE 6

Hu IL-2 Detection

| Ag (pg/ml) | Bio-Plex with 100% detection Ab | | | | | Signal Amp with 25% detection Ab | | | | |
|---|---|---|---|---|---|---|---|---|---|---|
| | FI | FI-Bkgd | % CV | Conc in Range | (Obs/Exp) * 100 | FI | FI-Bkgd | % CV | Conc in Range | (Obs/Exp) * 100 |
| 1144 | 3999 | 3984 | 5 | 1144 | 100 | 8597 | 8576 | 26 | 1215 | 106 |
| 290 | 1153 | 1138 | 0 | 290 | 101 | 2199 | 2179 | 3 | 275 | 96 |
| 68 | 271 | 256 | 4 | 68 | 96 | 570 | 549 | 16 | 62 | 87 |
| 19 | 89 | 74 | 0 | 19 | 108 | 235 | 214 | 17 | 23 | 126 |
| 4 | 36 | 21 | 1 | 4 | 93 | 63 | 42 | 2 | 4 | 92 |
| 1 | 27 | 12 | 8 | 1 | 104 | 35 | 14 | 2 | 1 | 129 |
| 0.29 | Undetected | | | 0 | | 22 | 2 | 13 | 0.35 | 124 |
| 0.07 | Undetected | | | 0 | | Undetected | | | 0 | |
| 0.02 | Undetected | | | 0 | | Undetected | | | 0 | |
| 0/Blank | 15 | 15 | 0 | 0 | | 21 | 21 | 0 | 0 | |
| Serum spike | | | | | | | | | | |
| 19 pg/ml | 67 | 52 | 3 | 13 | | 168 | 148 | 0 | 15 | |
| 4 pg/ml | 28 | 13 | 3 | 1 | | 59 | 39 | 0 | 4 | |
| 1 pg/ml | Undetected | | | 0 | | 29 | 9 | 0 | 0.9 | |
| CVD serum pool | Undetected | | | 0 | | 24 | 4 | 0 | 0.5 | |
| RA serum pool | Undetected | | | 0 | | 24 | 4 | 0 | 0.5 | |
| SLE serum pool | Undetected | | | 0 | | Undetected | | | 0 | |

Ag was spiked into serum collected from group of healthy human.
CVD serum was pooled from group of patients suffering from cardio vascular disease.
RA serum was pooled from group of patients suffering from rheumatoid arthritis disease.
SLE serum was pooled from group of patients suffering from systemic lupus erythematosus disease.

TABLE 7

Hu IL-4 Detection

| Ag (pg/ml) | Bio-Plex with 100% detection Ab | | | | | Signal Amp with 25% detection Ab | | | | |
|---|---|---|---|---|---|---|---|---|---|---|
| | FI | FI-Bkgd | % CV | Conc in Range | (Obs/Exp) * 100 | FI | FI-Bkgd | % CV | Conc in Range | (Obs/Exp) * 100 |
| 1144 | 2638 | 2622 | 6 | 1155 | 101 | 11711 | 11654 | 3 | 1234 | 108 |
| 290 | 586 | 570 | 1 | 283 | 99 | 2071 | 2014 | 7 | 255 | 89 |
| 68 | 140 | 124 | 0 | 70 | 97 | 533 | 476 | 2 | 70 | 97 |
| 19 | 45 | 29 | 6 | 18 | 102 | 196 | 139 | 18 | 23 | 128 |
| 4 | 23 | 7 | 5 | 5 | 115 | 85 | 28 | 1 | 5 | 110 |
| 1 | 18 | 2 | 4 | 1 | 113 | 65 | 8 | 2 | 1 | 110 |
| 0.29 | Undetected | | | 0 | | Undetected | | | 0 | |
| 0.07 | Undetected | | | 0 | | Undetected | | | 0 | |
| 0.02 | Undetected | | | 0 | | Undetected | | | 0 | |
| 0/Blank | 16 | 16 | 0 | 0 | | 57 | 57 | 0 | 0 | |
| Serum spike | | | | | | | | | | |
| 19 pg/ml | 36 | 20 | 0 | 13 | | 167 | 110 | 0 | 18 | |
| 4 pg/ml | 21 | 5 | 3 | 3.4 | | 71 | 14 | 0 | 2.4 | |
| 1 pg/ml | Undetected | | | 0 | | 74 | 17 | 0 | 3.0 | |
| CVD serum pool | Undetected | | | 0 | | 69 | 12 | 0 | 2.0 | |
| RA serum pool | Undetected | | | 0 | | Undetected | | | 0 | |
| SLE serum pool | Undetected | | | 0 | | Undetected | | | 0 | |

TABLE 8

| | Bio-Plex with 100% detection Ab | | | | | Signal Amp with 25% detection Ab | | | | |
|---|---|---|---|---|---|---|---|---|---|---|
| Ag (pg/ml) | FI | FI-Bkgd | % CV | Conc in Range | (Obs/Exp) * 100 | FI | FI-Bkgd | % CV | Conc in Range | (Obs/Exp) * 100 |
| 1144 | 1931 | 1912 | 2 | 2647 | 100 | 8610 | 8588 | 8 | 2328 | 106 |
| 290 | 601 | 583 | 8 | 646 | 98 | 2169 | 2147 | 4 | 498 | 91 |
| 68 | 193 | 175 | 7 | 171 | 104 | 694 | 672 | 22 | 137 | 100 |
| 19 | 62 | 44 | 5 | 39 | 96 | 225 | 203 | 20 | 37 | 107 |
| 4 | 33 | 14 | 9 | 11 | 106 | 78 | 56 | 27 | 9 | 110 |
| 1 | 24 | 6 | 9 | 2 | 94 | 30 | 8 | 4 | 2 | 79 |
| 0.29 | Undetected | | | 0 | | 22 | 0 | 2 | 1 | 124 |
| 0.07 | Undetected | | | 0 | | 18 | −4 | 20 | 0 | 106 |
| 0.02 | Undetected | | | 0 | | Undetected | | | 0 | |
| 0/Blank Serum spike | 19 | 19 | 4 | | | 22 | 22 | 0 | | |
| 19 pg/ml | 59 | 40 | 6 | 36 | | 220 | 198 | 0 | 36 | |
| 4 pg/ml | 30 | 11 | 2 | 8 | | 61 | 39 | 0 | 7 | |
| 1 pg/ml | Undetected | 4 | 9 | 0 | | 37 | 15 | 0 | 3 | |
| CVD serum pool | Undetected | 3 | 5 | 0 | | 24 | 2 | 0 | 1 | |
| RA serum pool | 27 | 8 | 4 | 5 | | 29 | 7 | 0 | 2 | |
| SLE serum pool | Undetected | | | 0 | | 37 | 15 | 0 | 3 | |

All documents (for example, patents, patent applications, books, journal articles, or other publications) cited herein are incorporated by reference in their entirety and for all purposes, to the same extent as if each individual document was specifically and individually indicated to be incorporated by reference in its entirety for all purposes. To the extent such documents incorporated by reference contradict the disclosure contained in the specification, the specification is intended to supersede and/or take precedence over any contradictory material.

Many modifications and variations of this invention can be made without departing from its spirit and scope, as will be apparent to those skilled in the art. The specific embodiments described herein are offered by way of example only and are not meant to be limiting in any way.

What is claimed is:

1. A method for detecting or quantifying an analyte in a sample, comprising in the following order:
    incubating the sample with a surface that is coated with a binding agent capable of binding to the analyte;
    incubating the surface with the same or a different binding agent of the analyte that is biotin-labeled;
    incubating the surface with unlabeled avidin or streptavidin;
    without removing the avidin or streptavidin, further incubating the surface with biotin labeled with a detectable label;
    washing the surface to remove reagents not bound to the surface; and
    detecting and/or quantitating the label and thereby detecting or quantifying the analyte.

2. The method of claim 1, wherein the surface is a bead.

3. The method of claim 2, wherein the beads are magnetically responsive.

4. The method of claims 2 or 3, wherein the beads are luminescent.

5. The method of claim 4, wherein more than one analyte binder is coated on a distinct set of beads with different luminescence.

6. The method of claim 1, wherein the surface is a microtiter plate well.

7. The method of claim 1, wherein the surface is a protein transfer membrane.

8. The method of claim 1, wherein the surface is a biological cell.

9. The method of claim 1, wherein the surface is a microscopy slide or a microfluidic chip.

10. The method of claim 1, wherein the molar ratio of avidin or streptavidin and labeled biotin is about 0.1:1 to 3:1.

11. The method of claim 10, wherein the molar ratio is about 0.3:1 to 1:1.

12. The method of claim 1, wherein the detectable label on biotin is a fluorophore, an enzyme, a radiolabel, an electron-dense reagent, a hapten or a protein.

13. The method of claim 12, wherein the fluorophore is phycoerythrin.

14. The method of claim 12, wherein the enzyme is horse radish peroxidase or alkaline phosphatase.

* * * * *